(12) United States Patent
Park et al.

(10) Patent No.: US 9,322,047 B2
(45) Date of Patent: Apr. 26, 2016

(54) METHODS OF AND DEVICES FOR CAPTURING CIRCULATING TUMOR CELLS

(71) Applicants: Taehyun Park, Baton Rouge, LA (US); Daniel Sang-Won Park, Baton Rouge, LA (US); Sudheer D Rani, Baton Rouge, LA (US); Michael C Murphy, Baton Rouge, LA (US); Dimitris E Nikitopoulos, Baton Rouge, LA (US)

(72) Inventors: Taehyun Park, Baton Rouge, LA (US); Daniel Sang-Won Park, Baton Rouge, LA (US); Sudheer D Rani, Baton Rouge, LA (US); Michael C Murphy, Baton Rouge, LA (US); Dimitris E Nikitopoulos, Baton Rouge, LA (US)

(73) Assignee: BOARD OF SUPERVISORS OF LOUISIANA STATE UNIVERSITY AND AGRICULTURAL AND MECHANICAL COLLEGE, Baton Rouge, LA (US)

( * ) Notice: Subject to any disclaimer, the term of this patent is extended or adjusted under 35 U.S.C. 154(b) by 0 days.

(21) Appl. No.: 13/656,295

(22) Filed: Oct. 19, 2012

(65) Prior Publication Data

US 2013/0109011 A1    May 2, 2013

Related U.S. Application Data

(60) Provisional application No. 61/552,522, filed on Oct. 28, 2011.

(51) Int. Cl.
*B01L 3/00* (2006.01)
*C12Q 1/24* (2006.01)
*G01N 33/569* (2006.01)
*G01N 33/574* (2006.01)

(52) U.S. Cl.
CPC ............. *C12Q 1/24* (2013.01); *B01L 3/502753* (2013.01); *G01N 33/56966* (2013.01); *G01N 33/574* (2013.01); *B01L 2200/0668* (2013.01); *B01L 2300/0816* (2013.01); *B01L 2300/0858* (2013.01); *B01L 2400/0487* (2013.01)

(58) Field of Classification Search
None
See application file for complete search history.

(56) References Cited

U.S. PATENT DOCUMENTS

| | | | | |
|---|---|---|---|---|
| 6,159,739 | A * | 12/2000 | Weigl et al. | 436/52 |
| 2005/0006238 | A1 * | 1/2005 | Jaffe | 204/450 |
| 2007/0099289 | A1 * | 5/2007 | Irimia | B01F 13/0066 435/287.2 |

FOREIGN PATENT DOCUMENTS

| WO | WO2007/110779 | * 10/2007 |
|---|---|---|
| WO | WO2009/140326 | * 11/2009 |

* cited by examiner

*Primary Examiner* — Melanie Y Brown
*Assistant Examiner* — Rebecca Martinez
(74) *Attorney, Agent, or Firm* — Jason P. Mueller; Adams and Reese LLP

(57) ABSTRACT

A device and methods are provided for efficient and quick capture of target cells through a main microchannel having capture elements immobilized thereon and manipulating a velocity profile of a sample as it passes through the main microchannel. The cell capture device may have a main microchannel with a depth slightly larger than the diameter of the target cells and a plurality of side microchannels. The side microchannels may have a depth smaller than the diameter of the target cells. The device and methods may be used for early cancer detection.

28 Claims, 7 Drawing Sheets

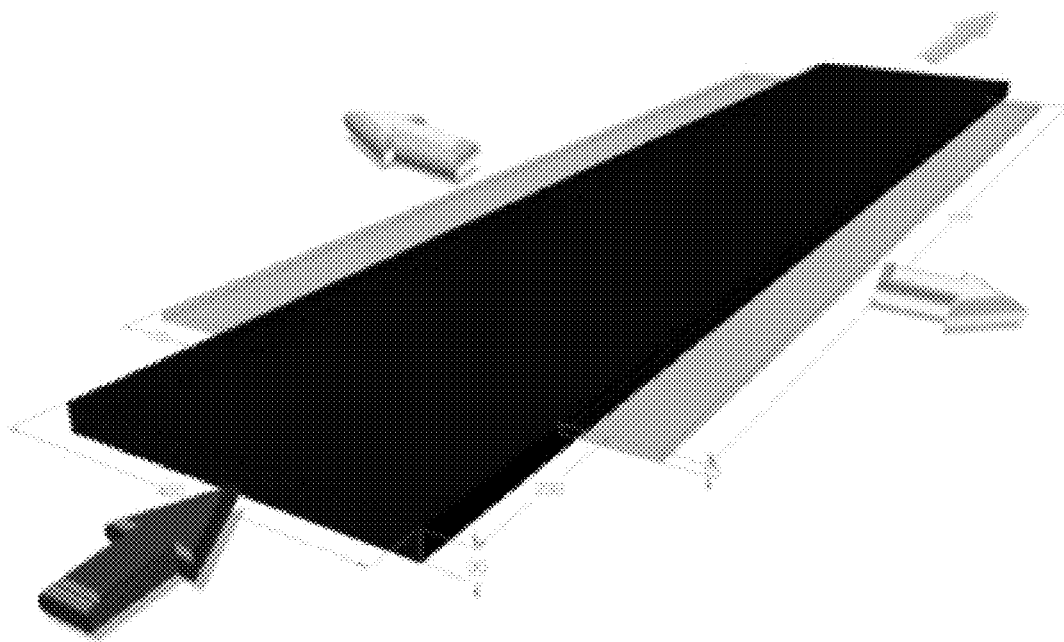
FIGURE 3
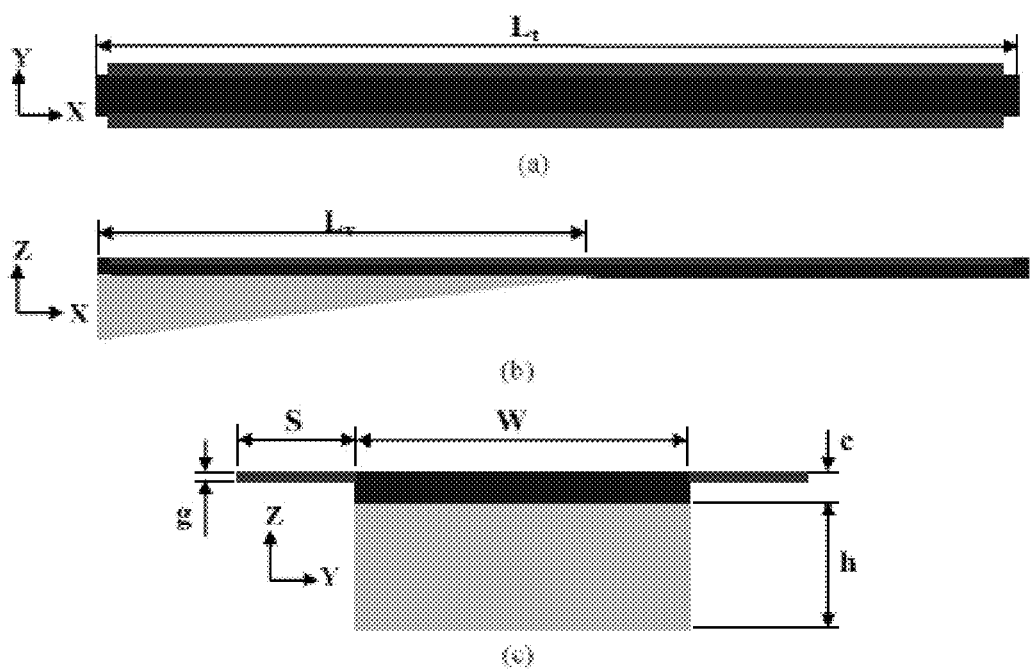
FIGURES 4(a), (b) and (c)

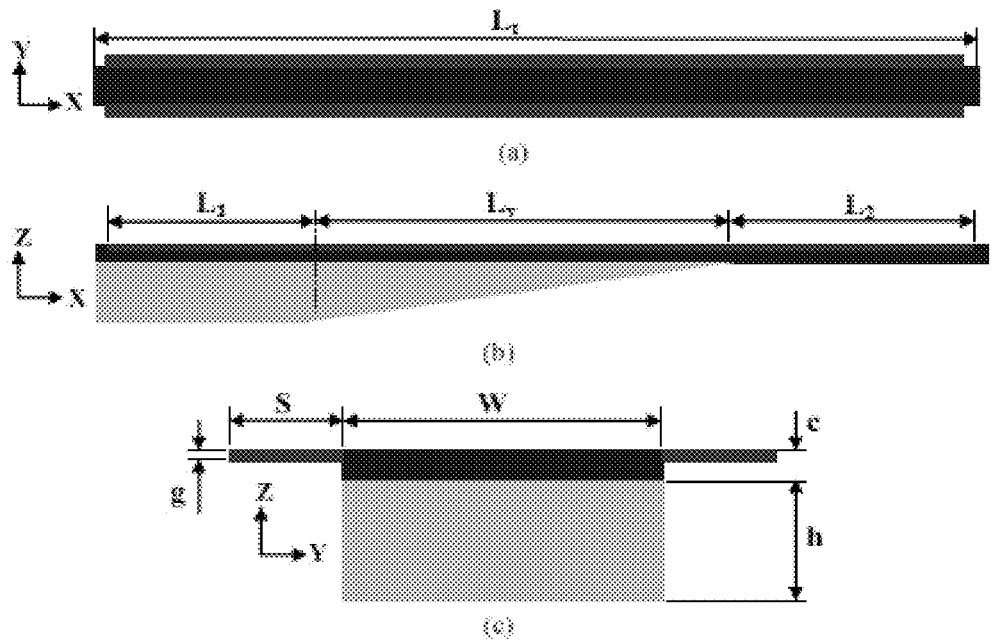
FIGURES 9 (a), (b), and (c)
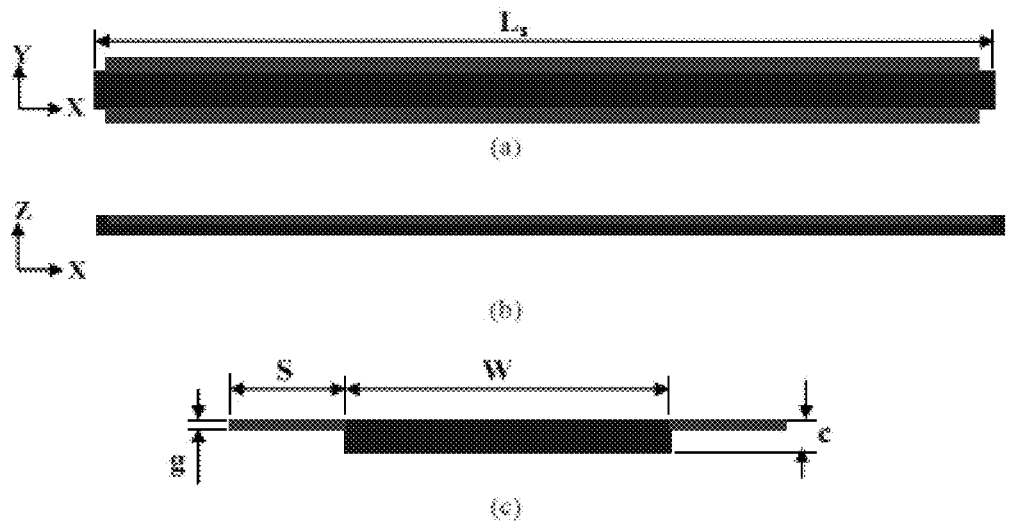
FIGURES 10 (a), (b), and (c)

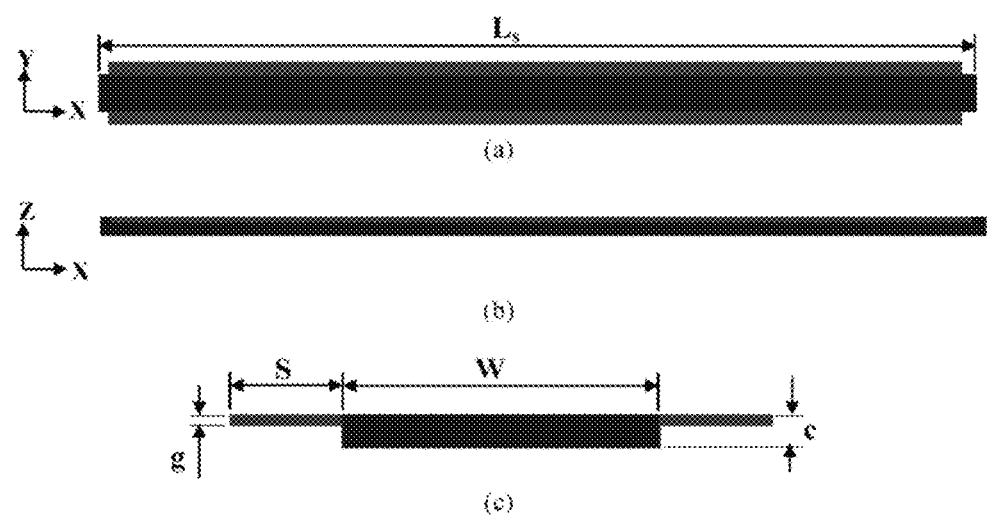
FIGURES 13 (a), (b), and (c)

METHODS OF AND DEVICES FOR CAPTURING CIRCULATING TUMOR CELLS

CROSS-REFERENCE TO RELATED APPLICATIONS

This application claims benefit of U.S. Provisional Application 61/552,522 filed Oct. 28, 2011, which is incorporated herein by reference.

STATEMENT REGARDING FEDERALLY SPONSORED RESEARCH OR DEVELOPMENT

This invention was made with government support under grant EPS 0346411 awarded by the National Science Foundation and grant R24 EB002115 awarded by the National Institutes of Health. The government has certain rights in the invention.

FIELD

The present invention relates to methods and devices for capturing cells, and in particular though non-limiting embodiments, to methods and devices for capturing circulating tumor cells.

BACKGROUND

Despite high compliance with screening programs there continues to be a high death rate from cancer. In the U.S., in 2010, there were an estimated 209,060 new cases of breast cancer diagnosed, with a mortality rate of about 20%. One problem with current screening programs is that existing methods detect cancer when it is too advanced to enable the use of optimal, less invasive treatment options. Early diagnosis of cancer is critical to reducing deaths resulting from the disease.

Existing methods for cancer detection vary depending on the organ affected. Current methods include biopsy, fecal occult blood testing, colonoscopy, computer-aided tomography, magnetic resonance imaging ("MRI"), x-ray mammography, and ultrasound. Current diagnostic technologies can only detect highly calcified tumors, can often be invasive, and are very expensive.

There are also methods known for detecting circulating tumor cells ("CTCs"). Due to the expression of specific mutations, CTCs allow the identification of the organ of origin and the stage of the disease. CTCs are an extremely rare occurrence of in human blood ($1:10^9$, or about 1 to about 2 CTCs in 1 mL of circulating blood). Detection of CTCs requires large sample volumes (about 7.5 mL), and current CTC-detection methods are slow, labor-intensive, and expensive.

Existing CTC detection methods generally involve BioMEMS technology (a subset of Micro Electro Mechanical System technology) and fall into one of three main categories: size-based, optically-based, and adhesion-based. Adhesion-based methods have high capture rates, however, flow rates must be reduced to provide sufficient time for the adhesion binding reaction to occur. Currently, adhesion based target cell capture devices use very low flow rates to increase capture rate, resulting in extended processing times.

Several studies have demonstrated CTC-capture using microfluidic devices to identify the presence of human breast cancer, and the CellSearch™ immunomagnetic system is approved by the Food and Drug Administration (FDA) for monitoring post-treatment therapy, but all of the systems reported have either a long diagnosis time or unacceptable capture rates.

Therefore, there is a long-standing but unmet need for methods and devices for detecting early-stage cancer, which can accurately, economically, and quickly detect the presence of cancer cells.

SUMMARY

In an example embodiment of the present disclosure, a device for capturing target cells is provided that includes: a main microchannel having a width, a depth, a length, an inlet and an outlet, wherein the depth is in the order of a diameter of the target cells; and at least one side microchannel connected to the main microchannel at at least one side microchannel inlet, each of the at least one side microchannel having a width, a depth and a length. The depth of each of the at least one side microchannel is sufficiently smaller than the diameter of the target cells such that the target cells cannot pass through the at least one side microchannel inlet. Capture elements are immobilized on at least one interior surface of the main microchannel.

The depth of the main microchannel may be slightly larger than the diameter of the target cells. The depth of the main microchannel may be slightly smaller than the diameter of the target cells. The device may have an overall length that is less than approximately 10 cm. The depth of each of the at least one side microchannel may be large enough to permit red blood cells to pass through the at least one side microchannel. The device may be thermoplastic molded. The device may be made of a polymer having a carboxyl group. The device may be made of Poly(methyl methacrylate). The device may be sealed by thermoplastic fusion bonding.

The target cells may be stem cells. The target cells may be bacteria cells. The target cells may be circulating tumor cells. The circulating tumor cells may be MCF-7 cells. The depth of the main microchannel may be approximately 30 µm. The depth of the main microchannel may be approximately 50 µm. The depth of each of the at least one side microchannel may be less than approximately 10 µm. The depth of each of the at least one side microchannel may be approximately 5 µm. The width of each of the at least one side microchannel may be approximately 100 µm. The width of the main channel may be between approximately 300 µm and approximately 500 µm. The depth of the main microchannel may be constant. A depth of a first portion of the main microchannel may be variable such that the depth may be larger at the inlet of the main microchannel and taper to the depth in the order of the diameter of the target cells. A depth of the first portion of the main microchannel may decrease from approximately 130 µm at the inlet of the main microchannel to approximately 30 µm.

The capture elements may be antibodies with affinity for an antigen of the target cells. The capture elements may be aptamers with affinity for an antigen of the target cells. The capture elements may be immobilized on a surface of the main microchannel near the at least one microchannel inlet. The device may also include at least one reservoir connected to each of the at least one side microchannel.

In an example embodiment of the present disclosure, a method of capturing target cells is provided that includes: passing a sample through a main microchannel having capture elements immobilized on at least one surface of the main microchannel; manipulating a velocity profile of the sample as it passes through the main microchannel such that the target cells move laterally in the main microchannel; and filtering non target cell portions of the sample out of the main microchannel. The size of a cross-section of the main microchannel is in the order of a diameter of the target cells such that an encounter rate between the target cells and the capture elements is increased. An inlet flow rate of the main microchannel is greater than an outlet flow rate of the main microchannel.

The inlet flow rate of the main microchannel may be approximately 0.75 µL/min. The outlet flow rate of the main microchannel may be approximately 1 mm/sec to approximately 2 mm/sec. The sample may be a fluid. The sample may be one of whole blood, urine, water, and a fecal sample. The non target cell portions of the sample may be filtered out using at least one side channel.

The capture elements may be one of antibodies and aptamers. The target cells may be stem cells. The target cells may be circulating tumor cells. The target cells may be bacteria cells.

In an example embodiment of the present disclosure, a cancer screening method is provided that includes: passing a sample through a device of claim 1. The cancer screening method may further include: collecting captured circulating tumor cells for further examination.

DESCRIPTION OF DRAWINGS

FIG. 3 is a conceptual representation a circulating tumor cell capture device, according example embodiment of the present invention.

FIG. 4(a) is a top view of the conceptual representation shown in FIG. 3.

FIG. 4(b) is a side view of the conceptual representation shown in FIG. 3.

FIG. 4(c) is a front view of the conceptual representation shown in FIG. 3.

FIG. 9(a) is a top view of a first section of the circulating tumor cell capture device shown in FIG. 8.

FIG. 9(b) is a side view of a first section of the circulating tumor cell capture device shown in FIG. 8.

FIG. 9(c) is a front view of a first section of the circulating tumor cell capture device shown in FIG. 8.

FIG. 10(a) is a top view of a second section of the circulating tumor cell capture device shown in FIG. 8.

FIG. 10(b) is a side view of a second section of the circulating tumor cell capture device shown in FIG. 8.

FIG. 10(c) is a front view of a second section of the circulating tumor cell capture device shown in FIG. 8.

FIG. 13(a) is a top view of a second section of the circulating tumor cell capture device shown in FIG. 11.

FIG. 13(b) is a side view of a second section of the circulating tumor cell capture device shown in FIG. 11.

FIG. 13(c) is a front view of a second section of the circulating tumor cell capture device shown in FIG. 11.

DESCRIPTION

In example embodiments of the present disclosure, two conflicting demands for capturing circulating tumor cells are balanced—shorter processing times (requiring higher flow rates) and the use of an affinity-based capture using antigen/antibody reactions (demanding sufficient time for the reactions to occur).

Figure 1:
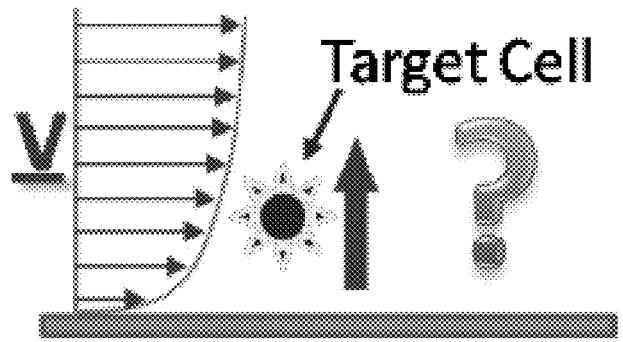
FIG. 1 is a representation of a fluid velocity profile near a wall of a single microchannel without a hole, according to an example embodiment of the present invention.
Figure 2:
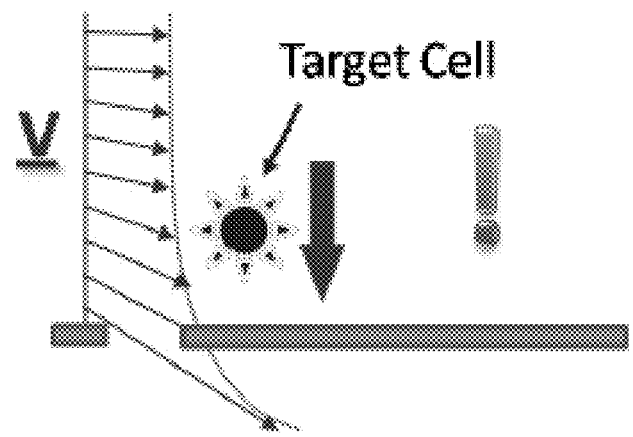
FIG. 2. is a representation of a fluid velocity profile near a wall of a single microchannel with a hole in the wall, according to an example embodiment of the present invention.

The low Reynolds number flows in most microchannels have a parabolic axial velocity profile that does not enable control of the lateral location of target cells. See FIG. 1. In example embodiments of the present disclosure, the velocity profile may be manipulated by introducing at least one side port on a main microchannel, which produces path lines directed toward the main microchannel wall. See FIG. 2.

The example embodiment in FIG. 3 shows a main microchannel having a 30 µm depth and a 400 µm width. In example embodiments, the depth of the main microchannel may be in the order of a diameter of the target cell. Where the depth is in the order of the diameter of the target cell, the depth may be similar or about the same as the diameter of the target cell. The depth may be slightly larger or slightly smaller than the diameter of the target cell. Side microchannels are provided in FIG. 3 having a depth of 10 µm. Alternative embodiments may have a single side microchannel or multiple side microchannels. A flow direction through the main microchannel is shown in FIG. 3 with arrows whereas a filter flow is shown flowing out into the side microchannels. FIGS. 4(a)-(c) provide dimensional views (top, side and front) of the embodiment shown in FIG. 3. Embodiments represented by FIG. 4(a)-(c) include a tapering first section wherein the main microchannel has a depth of h at the inlet and tapers to a depth of c after the first section.

In certain embodiments of the present invention, the height of the side microchannels is 5 µm for selective exclusion based on the size differences between human blood cells (<10 µm) and CTCs (>15 µm). In capture areas, axial velocities may be minimized (<2 mm/s) to obtain enough time for maximum CTC capture. In further embodiments of the present disclosure, lateral velocities on an exclusion path and contact location of the CTCs on the side channel entrance are also minimized to avoid target cell loss.

Figure 5:
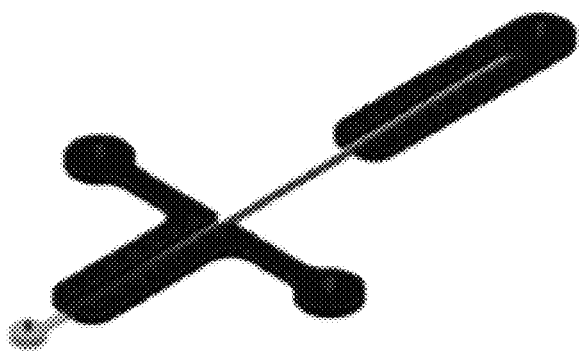
FIG. 5 is a design for a mold insert of a circulating tumor cell capture device, according to an example embodiment of the present invention.
Figure 6:
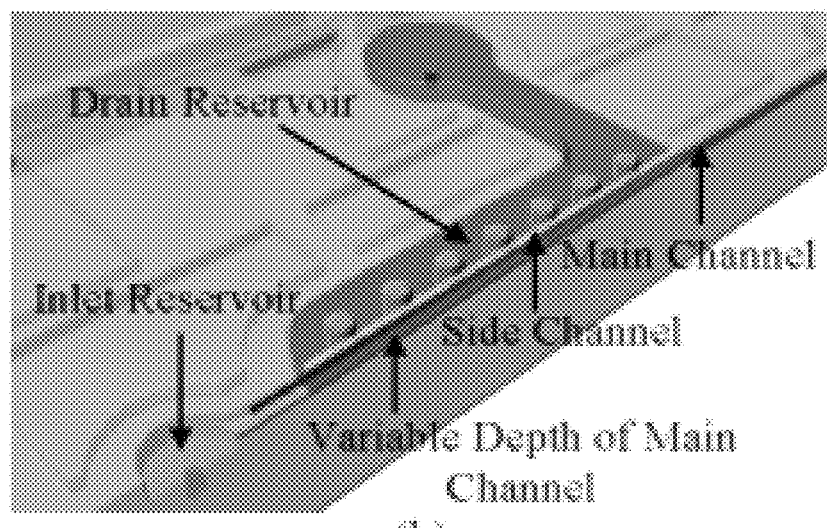
FIG. 6 is a partial view of a circulating tumor cell capture device, according to an example embodiment of the present invention.

In example embodiments of the present disclosure, a target cell capture device may be thermoplastic molded from a polymer having a carboxyl group, which may be polymethyl methacrylate (PMMA). PMMA is amenable to UV modification. See FIGS. 5 and 6. After UV exposure, the device may be amine functionalized, and antibodies (e.g. anti-EpCAM) may be immobilized on the microchannel surfaces. In other embodiments, aptamers may be immobilized on the microchannel surfaces. In example embodiments, the device may be sealed by thermoplastic fusion bonding. In certain embodiments, sealing may be completed with PMMA spin coated on a thin polycarbonate (PC) cover sheet to ensure minimum deformation of the depth of the side microchannels.

Figure 7:
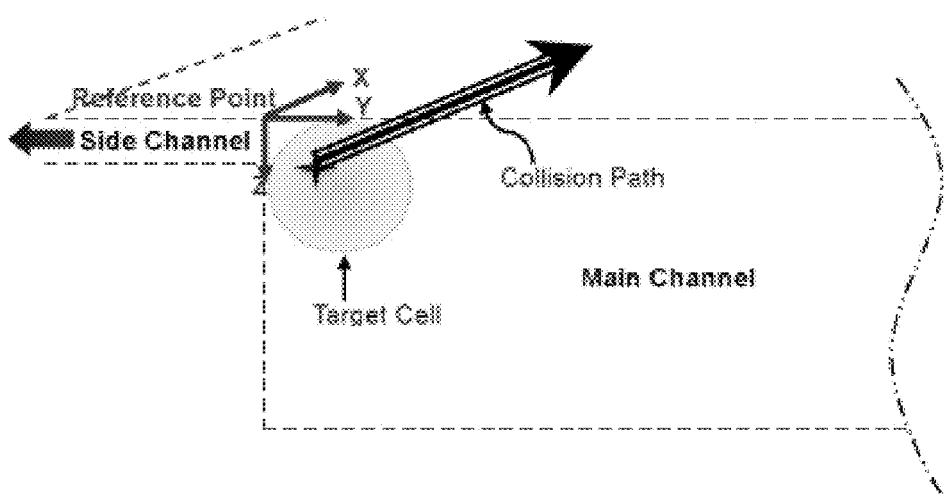
FIG. 7 is a cross sectional view of a main microchannel and a side channel, according to an example embodiment of the present invention.
Figure 8:
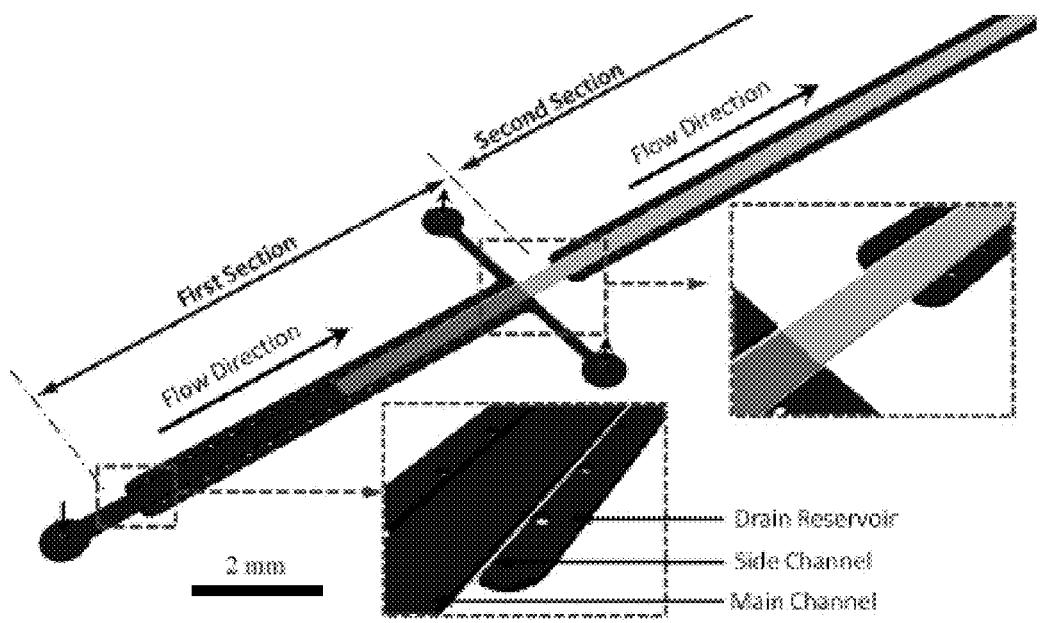
FIG. 8 is a schematic drawing of a circulating tumor cell capture device, according to an example embodiment of the present invention.
Figure 11:
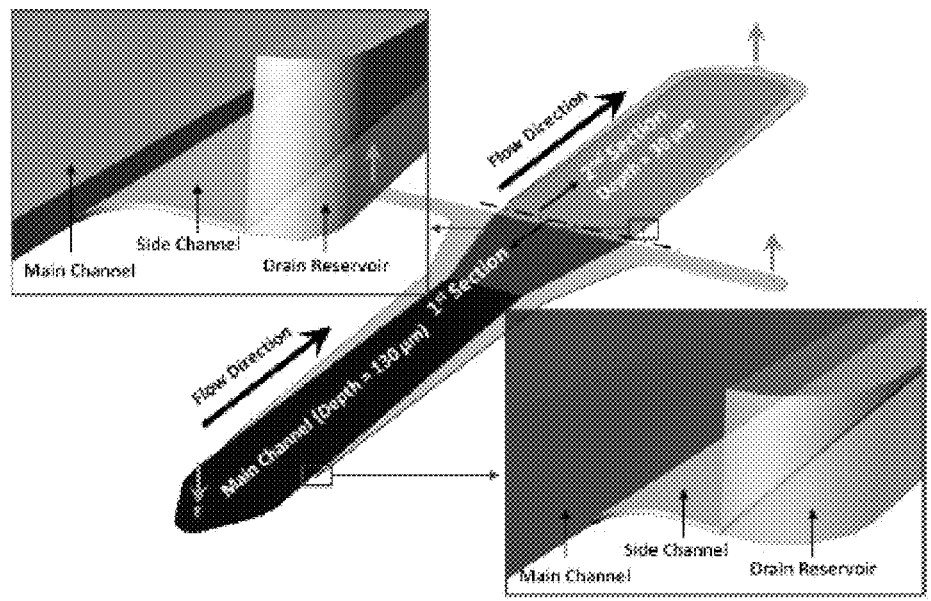
FIG. 11 is a schematic drawing of a circulating tumor cell capture device, according to an example embodiment of the present invention.
Figure 12:
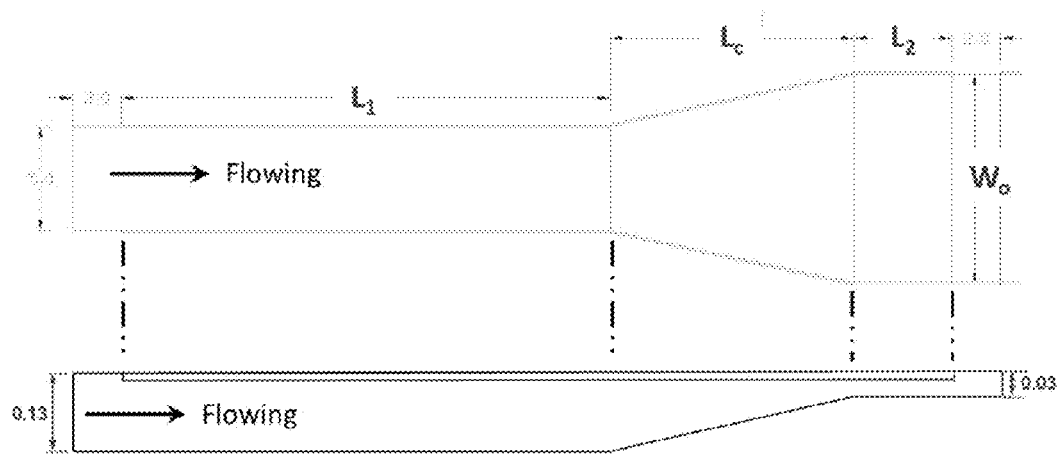
FIG. 12 is a side view and top view of a first section of the circulating tumor cell capture device shown in FIG. 11.

In further example embodiments of the present disclosure, a whole blood or a fecal sample is introduced into a target cell capturing device, and plasma, platelets, and red blood cells are size-filtered into parallel reservoirs on either side of a main microchannel. In example embodiments of the present disclosure, inlets for the side microchannels are small enough that the CTCs will not be drawn off, but about 95% or more of red blood cells will be. See FIG. 7. FIG. 7 shows a cross-section of a device including a main microchannel and a side microchannel. A target cell is shown which has a size too large to pass into the side microchannel.

In example embodiments of the present disclosure, a first section of a main microchannel is tapered, and followed by a second size filter to further reduce the concentration of red blood cells in the remaining sample. See FIGS. 8-13(c). Channel geometry in certain embodiments is tuned to give an exit velocity optimal for antibody-antigen based capture of the CTCs. In example embodiments of the present disclosure, the capture section is about the height of a CTC, but wide enough to be manufacturable and have an acceptably small pressure drop. In further embodiments of the present disclosure, the walls are functionalized with capture elements, either antibodies or aptamers may be used, to separate target cells from the flow with high sensitivity.

In example embodiments of the present disclosure, cells may be enumerated using fluorescent dyes and a fluorescence microscope. In certain embodiments, cells may be enumerated using a conductivity sensor. In still other embodiments of the present disclosure, the device may be coupled with an analytical platform for mutation detection.

Sample Preparation

Test samples were prepared by isolating live CTCs and staining them with membrane fluorescence. After staining, the CTCs were spiked in red blood cells (RBCs) using a dilution method. The CTCs, spiked with RBCs, were driven through a device with a syringe pump at 150 µL/min flow. The RBCs passed freely through side microchannel inlets and were excluded because of their high deformability and small size. The CTCs could not escape through the side microchannel inlets but were captured by antibodies immobilized on a main microchannel surface, near the side microchannel inlets in most cases. The captured CTCs were counted after a PBS rinse to remove any nonspecific binding material from the main microchannel. CTCs were captured using the device at an average 81% capture rate in RBCs. The results showed the highest flow rate for efficient affinity-based CTC capture to date.

The dimensions of the side microchannels and the magnitude of the lateral velocity are very important because the target cells can deform and escape through the side channel. Escape velocity depends on cell properties (size, type, or shape) and the side channel geometry. To avoid the loss of rare target cells and to filter other blood cells selectively, dimensions of the side microchannels are determined based on the size and deformability differences between the target cells and blood cells. For breast cancer, the target cells, CTCs, are typically 15-30 µm in diameter and blood cells are usually less than 10 µm. Therefore, the side microchannels need to be less than 10 µm which also depends on the escape velocity or pressure gradient at the near the side microchannels. In example embodiments, a velocity in the main channel is minimized (<2 mm/s) to maximize duration time of the antigen/antibody binding and to avoid target cell loss through the main microchannel outlet at the end. In example embodiments, the device has two sections to manipulate the axial and lateral velocities in each section individually. A first section has variable depth of main microchannel, reducing the depth from 130 µm to 30 µm. A second section, with a 30 µm deep main microchannel, has an enlarged width to help decrease the velocity.

Multiple cases of geometries/dimensions were simulated using Fluent v6.3 to optimize the design. Boundary conditions were inlet velocity and outlet pressure (atmosphere pressure). The working fluid was water. An inlet flow rate of 0.75 mL/min was specified to process 7.5 mL in 10 minutes. Two parameters were investigated, the axial velocity to ensure enough encounter time for binding and exclusion velocity, lateral velocity of the target cell at the moment of exclusion, to avoid target cell loss. The exclusion velocity was extracted along an exclusion path-line that was 5 µm away from the side channel in the main microchannel.

In alternative embodiments, the device is configured as a front-end processor for a modular, multi-well microfluidic analytical system. The device may be fit into an 8 mm×8 mm footprint of a single well on the standard micro-titer plate. CTCs are captured from 96 samples in parallel and analyzed for mutations or other characteristics.

In further embodiments of the present invention, the device is used to capture stem cells from solution, which streamlines processes for handling and separating stem cells. In certain embodiments, the device may be used to capture bacteria cells from a sample.

While the embodiments are described with reference to various implementations and exploitations, it will be understood that these embodiments are illustrative and that the scope of the inventions is not limited to them. Many variations, modifications, additions, and improvements are possible. Further still, any steps described herein may be carried out in any desired order, and any desired steps may be added or deleted.

What is claimed is:

1. A device for capturing target cells, comprising:
    a main microchannel having a first portion, a second portion, an inlet and an outlet, the first portion having a first portion depth that is larger at the inlet of the main microchannel and tapers to a depth in the order of the diameter of the target cells along the length of the first portion, the second portion having a second portion width that is smallest at a connection with the first portion and that increases along a second portion length of the second portion, the second portion having a second portion depth in the order of a diameter of the target cells; and
    at least two side microchannels connected to the main microchannel on opposite sides of the first portion of the main microchannel, each of the at least two side microchannels having a side microchannel width, a side microchannel depth and a side microchannel length,
    wherein the side microchannel depths are sufficiently smaller than the diameter of the target cells such that the target cells cannot pass through the at least two side microchannels,
    wherein a capture elements is immobilized on at least one interior surface of the main microchannel.

2. The device of claim 1, wherein the second portion depth of the main microchannel is slightly larger than the diameter of the target cells.

3. The device of claim 1, wherein the device has an overall length that is less than approximately 10 cm.

4. The device of claim 1, wherein the side microchannel depth of each of the at least two side microchannels is large enough to permit red blood cells to pass through the at least two side microchannels.

5. The device of claim 1, wherein the device is molded thermoplastic.

6. The device of claim 5, wherein the device is made of a polymer having a carboxyl group.

7. The device of claim 5, wherein the device is made of Poly(methyl methacrylate).

8. The device of claim 5, wherein the device is sealed by thermoplastic fusion bonding.

9. The device of claim 1, wherein the target cells are stem cells.

10. The device of claim 1, wherein the target cells are bacteria cells.

11. The device of claim 1, wherein the target cells are circulating tumor cells.

12. The device of claim 11, wherein the circulating tumor cells are MCF-7 cells.

13. The device of claim 1, wherein the second portion depth of the main microchannel is approximately 30 µm.

14. The device of claim 1, wherein the second portion depth of the main microchannel is approximately 50 µm.

15. The device of claim 1, wherein the side microchannel depth of each of the at least two side microchannels is less than approximately 10 µm.

16. The device of claim 1, wherein the side microchannel depth of each of the at least two side microchannels is approximately 5 µm.

17. The device of claim 1, wherein the side microchannel width of each of the at least two side microchannels is approximately 100 µm.

18. The device of claim 1, wherein the width of the second portion of the main channel is between approximately 300 µm and approximately 500 µm.

19. The device of claim 18, wherein the first portion depth of the first portion of the main microchannel decreases from approximately 130 µm at the inlet of the main microchannel to approximately 30 µm.

20. The device of claim 1, wherein the capture elements are antibodies with affinity for an antigen of the target cells.

21. The device of claim 1, wherein the capture elements are aptamers with affinity for an antigen of the target cells.

22. The device of claim 1, wherein the capture elements are immobilized on a surface of the main microchannel near at least one of the at least two side microchannels inlet and the main microchannel outlet.

23. The device of claim 1, further comprising: at least one reservoir connected to each of the at least two side microchannels.

24. A cancer screening method, comprising: passing a sample through a device of claim 1.

25. The cancer screening method of claim 24, further comprising: collecting captured circulating tumor cells for further examination.

26. The device of claim 1, wherein the device is configured to direct the main flow towards the sides of the main microchannel.

27. The device of claim 1, wherein each side microchannel further includes an exit flow at a position perpendicular to the flow of the main microchannel.

28. The device of claim 1, wherein each side microchannel includes a side channel and a drain reservoir portion, the drain reservoir portion having a greater height than the side channel portion.

* * * * *